United States Patent [19]

Angres

[11] Patent Number: 5,157,151

[45] Date of Patent: Oct. 20, 1992

[54] SALTS OF 1-ADAMANTAMINE AND FORMULATIONS THEREOF

[76] Inventor: Isaac Angres, 6 War Admiral Ct., Gaithersburg, Md. 20878

[21] Appl. No.: 629,557

[22] Filed: Dec. 18, 1990

[51] Int. Cl.$^5$ ..................... C07C 229/00; C07C 62/06
[52] U.S. Cl. .................................. 562/466; 562/468; 562/458
[58] Field of Search ........................ 562/458, 466, 468

[56] References Cited

U.S. PATENT DOCUMENTS 4,551,463  11/1985  Sherlock .............................. 514/300

OTHER PUBLICATIONS

Physicians Desk Reference 1977 p. 1676.

*Primary Examiner*—Paul J. Killos
*Attorney, Agent, or Firm*—Isaac Angres

[57] ABSTRACT

Novel salts of 1-adamantamine are formed by reacting non-steroidal anti-inflammatory carboxylic acids with 1-adamantamine. Formulations of 1-adamantamine hydrochloride and non-steroidal anti-inflammatory carboxylic acids are also described.

5 Claims, No Drawings

SALTS OF 1-ADAMANTAMINE AND FORMULATIONS THEREOF

The present invention relates to novel salts of 1-adamantamine prepared by reacting adamantamine with non-steroidal anti-inflammatory carboxylic acids such as the acetic acids and the propionic acids.

DESCRIPTION OF THE PRIOR ART

Adamantamine is a well known antiviral agent described in U.S. Pat. No. 3,152,180. The use of adamantamine to treat influenza A viral infections as well as its use profilactically as an antiviral is well described in the literature. See *Toxicol. Appl. Pharmacol.* 15, 642 (1969).

Non-steroidal anti-inflammatory carboxylic acids such as those of the salicylic, acetic, propionic, biphenyl, and diphenylether series are also well known in the literature. Some of them have been reported to also have anti-viral properties. Typical acids include ibuprofen, naproxyn, aspirin, as well as all those listed in U.S. Pat. No. 4,552,899 whose contents are incorporated by reference herein.

The chemical structure of adamantamine is:

SUMMARY OF THE INVENTION

The primary object of the present invention is to provide novel salts of adamantamine by reacting adamantamine with non-steroidal anti-inflammatory carboxylic acids.

Another object of the present invention is to provide pharmaceutical compositions of matter comprising adamantamine or its salts and non-steroidal anti-inflammatory carboxylic acids.

DESCRIPTION OF THE PREFERRED EMBODIMENTS

The present invention deals with compounds having the following formula:

wherein R represents the chemical moiety derived from a non-steroidal anti-inflammatory carboxylic acid.

The compounds of the present invention are prepared by reacting adamantamine with a non-steroidal carboxylic acid in a solvent such as ethanol either at room temperature or under reflux conditions. After reaction, the solvent is evaporated to give the novel salts of the invention.

The preferred non-steroidal carboxylic acids include the salicylic acids, the acetic acids, the fenamic acids, the propionic acids and the biphenyl carboxylic acids. Typical acids include ibuprofen, diflunisal, fenoprofenic acid, meclofenic acid, mefenamic acid, naproxen, sulindac, indomethacin, tolmetin, fenbufen, ketoprofen, indoprofen, fluprofen, benozaprofen, pirprofen, miroprofen and trioxaprofen.

In another embodiment of the present invention, adamantamine or its salts are blended with the non-steroidal anti-inflammatory carboxylic acids to give novel pharmaceutical compositions. For example adamantamine hydrochloride can be blended with ibuprofen to give a novel formulation useful in treating influenza A infections.

EXAMPLE 1

The following is a general method for making the salts of the present invention: 0.1 mole of a non-steroidal carboxylic acid and 0.1 mole of 1-adamantamine are dissolved in 200 mls of pharmacologic grade ethanol. The solution is refluxed for 30 minutes and then the ethanol is evaporated under vacuum. The resulting salt is then washed several times with ether and then dried.

EXAMPLE 2

Following the procedure of Example 1, ibuprofen (0.1 mole) is reacted with 1-adamantamine (0.1 mole) to produce 1-adamantamine ibuprofenate.

EXAMPLE 3

100 mg of adamantamine hydrochloride are mixed with 200 mg of ibuprofen. The active ingredients are triturated and q.s. with lactose to selected capsule size.

It is to be understood that the forms of the invention herewith are to be taken as preferred examples of the same, and that various changes may be made without departing from the spirit of the invention or scope of the subjoined claims.

I claim:

1. A pharmaceutical compound of the formula wherein $$R-\overset{O}{\underset{\|}{C}}-O^-$$

represents a non-steroidal anti-inflammatory carboxylic acid selected from the group comprising the anti-inflammatory substituted and unsubstituted aryl acetic acids, the anti-inflammatory substituted and unsubstituted aryl propionic acids, the fenamic acids and the biphenyl carboxylic acids.

2. The compositions of claim 1 where $$R-\overset{O}{\underset{\|}{C}}-O^-$$

is ibuprofen.

3. The composition of claim 1 where

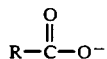

is naproxyn.

4. A pharmaceutical composition of matter comprising adamantamine hydrochloride and a non-steroidal anti-inflammatory carboxylic acid selected from the group of substituted and unsubstituted aryl acetic acids, substituted and unsubstituted aryl propionic acids, the fenamic acids and the biphenyl carboxylic acids.

5. 1-Adamantamine Ibuprofenate.

* * * * *